(12) United States Patent
Lei et al.

(10) Patent No.: US 8,722,933 B2
(45) Date of Patent: May 13, 2014

(54) METHOD FOR PREPARING METAL COMPLEXES OF POLYDENTATE BETA-KETOIMINATES

(75) Inventors: Xinjian Lei, Vista, CA (US); Daniel P. Spence, Carlsbad, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 391 days.

(21) Appl. No.: 12/702,655

(22) Filed: Feb. 9, 2010

(65) Prior Publication Data

US 2011/0040124 A1    Feb. 17, 2011

Related U.S. Application Data

(60) Provisional application No. 61/159,237, filed on Mar. 11, 2009.

(51) Int. Cl.
C07C 249/00    (2006.01)
C07C 251/00    (2006.01)

(52) U.S. Cl.
USPC ........................................................ 564/279

(58) Field of Classification Search
None
See application file for complete search history.

(56) References Cited

U.S. PATENT DOCUMENTS

| | | | |
|---|---|---|---|
| 4,982,019 A * | 1/1991 | Purdy et al. | 568/842 |
| 6,552,209 B1 | 4/2003 | Lei et al. | |
| 2007/0248754 A1 | 10/2007 | Lei et al. | |

FOREIGN PATENT DOCUMENTS

| | | |
|---|---|---|
| JP | 6-298714 | 10/1994 |
| JP | 2009-007333 | 1/2009 |
| JP | 2009-161513 | 7/2009 |
| JP | 2010-111672 | 5/2010 |
| WO | 2004002946 | 1/2004 |

OTHER PUBLICATIONS

T. Chou, et al, Synthesis and Characterization of Tris(B-ketoiminato)ruthenium(III) Complexes: Potential Precursors for CVD of Ru and RuO2 Thin Films, Chemical Vapor Deposition, 2004, 149-158.
N. Edleman, et al, Synthesis and Characterization of Volatile, Fluorine-Free B-Ketoiminate Lanthanide MOCVD Precursors and Their Implementation in Low-Temperature Growth of Epitaxial CeO2 Buffer Layers for Superconducting Electronics, Inorganic Chemistry, 2002, 5005-5023.
J. Matthews, et al, Group 2 Element Precursors for the Chemical Vapor Deposition of Electronic Materials, Advances in Inorganic Chemistry, 2000, 173-192.
S. Pasko, et al, Synthesis and characterization of new alkaline earth metal B-ketoiminates. The first structurally characterized strontium B-ketoiminate, Inorganic Chemistry Communications, 2005, 483-487.
D. Schulz, et al, New Precursors for Barium MOCVD. B-Ketoiminate Complexes Containing Appended Polyether "Lariats", Inorganic Chemistry, 1993, 249-250.
I. Lee, Characteristics and Applications of Metal Complexes with B-Ketoiminate Ligands, Focus on Organometallic Chemistry Research, 2005, 133-145.

* cited by examiner

*Primary Examiner* — Johann R Richter
*Assistant Examiner* — Jennifer C Sawyer
(74) *Attorney, Agent, or Firm* — Rosaleen P. Morris-Oskanian; Joseph D. Rossi

(57) ABSTRACT

A method for making a group 2 metal-containing polydentate β-ketoiminate represented by the following structure A:

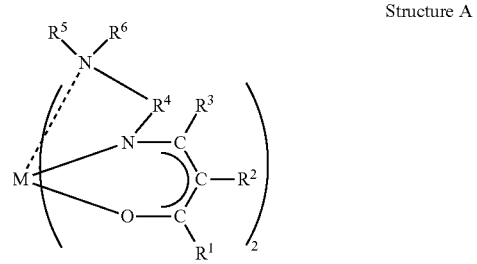

Structure A wherein M is a metal selected from the group consisting of Mg, Ca, Sr, and Ba; $R^1$, $R^3$, $R^5$, and $R^6$ are independently selected from an alkyl group, a fluoroalkyl group, a cycloaliphatic group, and an aryl group; $R^2$ is selected from a hydrogen atom, an alkyl group, an alkoxy group, a cycloaliphatic group, and an aryl group; and $R^4$ is an alkyenyl bridge, comprising: reacting M in a reaction mixture comprising a tridentate ketoimine ligand and an alcohol comprising at least one selected from the group consisting of $R^7OH$ and $(OH)_nR^8$ wherein $R^7$ and $R^8$ are independently selected from an alkyl group and an aryl group. In certain embodiments, the reaction mixture further comprises an organic solvent.

17 Claims, No Drawings

METHOD FOR PREPARING METAL COMPLEXES OF POLYDENTATE BETA-KETOIMINATES

CROSS-REFERENCE TO RELATED APPLICATIONS

This application claims the priority benefit of U.S. Provisional Application No. 61/159,237, filed 11 Mar. 2009.

BACKGROUND OF THE INVENTION

The semiconductor fabrication industry continues to need metal source containing precursors for chemical vapor deposition processes including atomic layer deposition for fabricating conformal metal containing films on substrates such as silicon, metal nitride, metal oxide and other metal-containing layers using these metal-containing precursors. To this end, a method for preparing metal source containing precursors with a yield that is higher relative than previous preparation methods and, in certain instances, a cost that is lower than previous methods would be desirable to the semiconductor fabrication industry. Also desirable is a method for preparing these precursors whereby the metal source containing precursor is prepared while minimizing potential metal impurities that may be introduced during the preparation process, such as but not limited to, lithium, sodium, potassium and combinations thereof.

Previous methods for preparing polydentate β-ketoiminate ligands were performing using well known procedure such as the Claisen condensation of a bulky ketone and an ethyl ester in presence of a strong base such as sodium amide or hydride, followed by another known procedure such as Schiff base condensation reaction with alkylaminoalkylamine such as that shown below in the multi-step scheme depicted below as Equation 1:

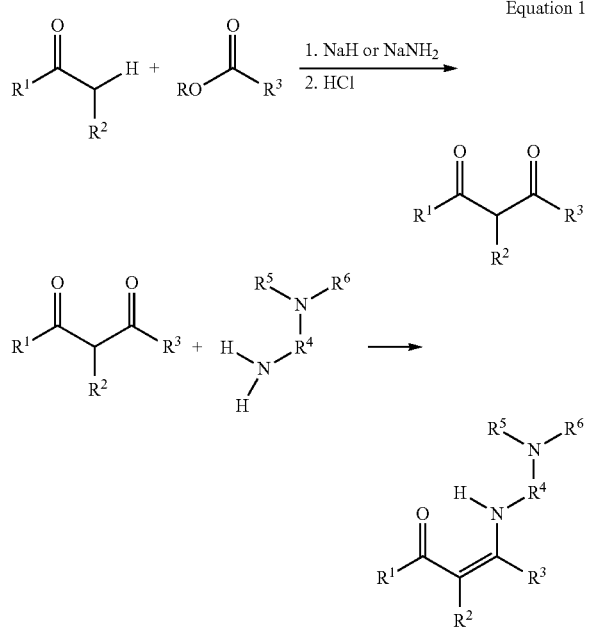

Equation 1

Another method for preparing the metal-containing complexes involved reacting tridentate β-ketoiminate ligands with group 2 metal in the presence of ammonia, metal amide, metal hydride, or metal alkoxide such as that shown below in Equation 2.

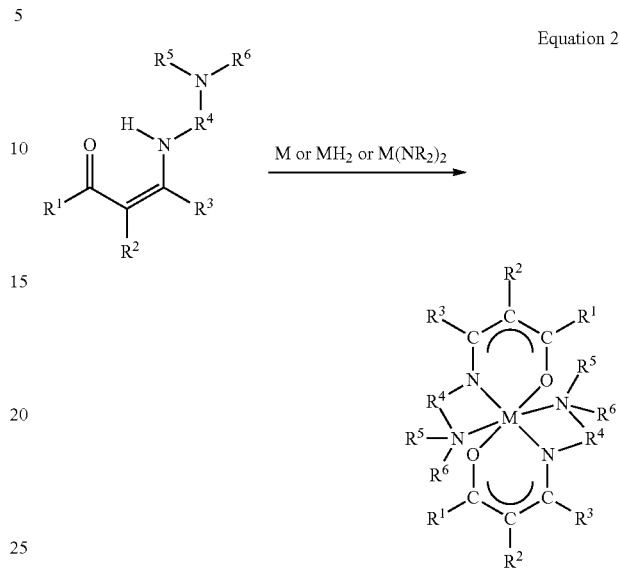

Equation 2

The metal-containing complexes can also be prepared via reacting the polydentate β-ketoiminate ligand with alkyl lithium or potassium hydride to provide the lithium or potassium salt of the ligand, then followed by reaction with a metal halide having the formula $MX_2$ (X=Cl, Br, I) such as that shown below in Equation 3:

Equation 3

However, the reaction such as Equation 2 using group 2 metals in the presence of ammonia may not be suitable for larger scale processing because bubbling ammonia is tedious process and the reaction yields are typically very low. Further, reactions such as Equation 1 and 3 involving sodium or potassium hydride as reagents are undesirable because of their high reactivity which can cause potential fire in addition to sodium or potassium impurities in the final product. Still other reactions that employ metal amides or alkoxides as reagents such as Equation 2 are not practical because the reagents are too expensive.

BRIEF SUMMARY OF THE INVENTION

Described herein is a method for preparing group 2 metal-containing polydentate β-ketoiminates wherein the polydentate β-ketoiminates incorporate nitrogen or oxygen functionality in the imino group. In one embodiment, the group 2 metal polydentate β-ketoiminates are selected from the group represented by the following structure A:

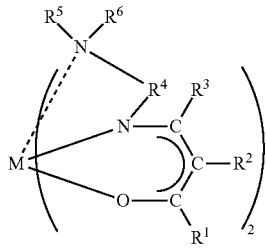

Structure A

In structure A, M is a metal selected from the group consisting of Mg, Ca, Sr, and Ba; $R^1$, $R^3$, $R^5$, and $R^6$ are independently selected from an alkyl group, a fluoroalkyl group, a cycloaliphatic group, and an aryl group; $R^2$ is selected from a hydrogen atom, an alkyl group, an alkoxy group, a cycloaliphatic group, and an aryl group; and $R^4$ is an alkyenyl bridge. In one embodiment, $R^4$ is an alkyenyl bridge such as, but not limited to, a group containing 2 or 3 carbon atoms, thereby making a five- or six-member coordinating ring to the metal center. In this or other embodiments, any one or more of substituents $R^1$, $R^2$, $R^3$, $R^5$, and $R^6$ can be connected to form a ring. In this or other embodiments, the ring may further comprise carbon, oxygen, and/or nitrogen atoms.

In one aspect, there is provided a method for making a group 2 metal-containing polydentate β-ketoiminate represented by the following structure A:

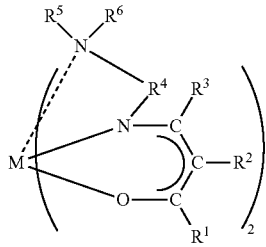

Structure A wherein M is a metal selected from the group consisting of Mg, Ca, Sr, and Ba; $R^1$, $R^3$, $R^5$, and $R^6$ are independently selected from an alkyl group, a fluoroalkyl group, a cycloaliphatic group, and an aryl group; $R^2$ is selected from a hydrogen atom, an alkyl group, an alkoxy group, a cycloaliphatic group, and an aryl group; and $R^4$ is an alkyenyl bridge, comprising: reacting M in a reaction mixture comprising a tridentate ketoimine ligand and an alcohol comprising at least one selected from the group consisting of $R^7OH$ and $(OH)_nR^8$ wherein $R^7$ and $R^8$ are independently selected from an alkyl group and an aryl group. In certain embodiments, the reaction mixture further comprises an organic solvent.

At least one of the following advantages can be achieved by the method described for preparing the metal-containing polydentate β-ketoiminates and may include:

an ability to form reactive metal-containing polydentate β-ketoiminates at a yield higher than previously available preparation methods;
 an ability to eliminate potential metal impurities in the metal-containing polydentate β-ketoiminates such as, but not limited to, lithium, sodium, or potassium;
 an ability to eliminate potential halide impurities in the metal-containing polydentate via using pure metal instead of metal halide in previous methods; and/or
 an ability to simplify the process, thereby reducing the cost of manufacture.

DETAILED DESCRIPTION OF THE INVENTION

The process described herein is a process for preparation of group 2 metal-containing polydentate β-ketoiminates that may avoid yield losses, slow reaction time, and/or the introduction of impurities problems into the end product. The process described herein avoids these problems by introducing a metal, such as, for example, a pure group 2 metal, an alcohol, and a tridentate ketoimine ligand into the reaction mixture. It is believed that the presence of the alcohol within the reaction mixture forms a metal alkoxide in situ which further reacts with the tridentate ketoiminate ligand to form the polydentate β-ketoiminate end-product. Previous preparation methods taught that it was not possible to make metal containing polydentate β-ketoiminates, particularly strontium complexes, using pure Sr metal as starting material. Thus, it is surprising and unexpected to prepare metal-containing polydentate β-ketoiminates complexes such as strontium complexes using a reaction mixture comprising Sr metal, one or more alcohols such as isopropyl alcohol (IPA), and a tridentate ketoimine ligand to provide the end-product at a relatively high yield such as greater than 80%. In certain embodiments, the group 2 metal, such as the Sr metal, is a pure metal. The term "pure" as used herein means comprising 99% or greater of the group 2 metal determined by inductively coupled plasma mass spectroscopy (ICP-MS).

The process described herein provides one or more or following advantages over other methodologies presently available. First, the process may permit the use of relatively lower cost reagents. For example, in certain embodiments, the process may use a group 2 metal rather than the commonly used reagent such as group 2 metal amides. At the present time, the group 2 metal in its pure form is more cost effective than metal amides which are typically prepared via reaction between metal halides and sodium or potassium amides. Second, the process described herein may avoid the use of a sodium or potassium hydride to form group 2 metal amides. Instead, in the process described herein, the by-product of the reaction of the pure group 2 metal and the tridentate ketoimine is hydrogen which is more easily removed from the end product mixture and/or is not a detrimental impurity within the end product mixture. It is believed that the alcohol provides a reflux within the reactive mixture during the reaction to form reactive group 2 metal alkoxides in situ and further reacts with the tridentate ketoimine ligand thereby generating the final product. In certain embodiments, the alcohol and the unreacted tridentate ketoimine ligand, and the solvent can be easily removed from the reaction mixture using distillation, fractionation, stripping, or other means.

The group 2 metal-containing polydentate β-ketoiminates are selected from the group represented by the following structure A:

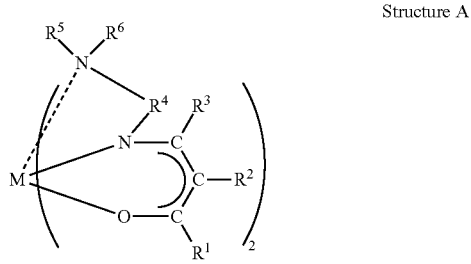

Structure A

In Structure A, M is a metal selected from the group consisting of Mg, Ca, Sr, and Ba; $R^1$, $R^3$, $R^5$, and $R^6$ are independently selected from an alkyl group, a fluoroalkyl group, a cycloaliphatic group, and an aryl group; $R^2$ is selected from a hydrogen atom, an alkyl group, an alkoxy group, a cycloaliphatic group, and an aryl group; and $R^4$ is an alkyenyl bridge. In Structure A and throughout the description, the term "alkyl" denotes a linear, branched, or cyclic functional group having from 1 to 20, or from 1 to 12 or from 1 to 6 carbon atoms. Exemplary alkyl groups include, but are not limited to, methyl, ethyl, propyl, isopropyl, butyl, isobutyl, sec-butyl, tert-butyl, pentyl, hexyl, octyl, decyl, dodecyl, tetradecyl, octadecyl, isopentyl, and tert-pentyl. The term "alkyl" also applies to alkyl moieties contained in other groups such as haloalkyl, fluoroalkyl, alkaryl, or aralkyl. In Structure A and throughout the description, the term "fluoroalkyl" denotes a linear, branched, or cyclic functional group having from 1 to 20, or from 1 to 12 or from 1 to 6 carbon atoms and at least one fluorine atom. In Structure A and throughout the description, the term "cycloaliphatic group" denotes a group that is aliphatic and comprises at least one cyclic group which is saturated or unsaturated having from 3 to 20, or from 3 to 12 or from 3 to 6 carbon atoms. In Structure A and throughout the description, the term "aryl" denotes a cyclic functional group having from 6 to 12 carbon atoms. Exemplary aryl groups include but are not limited to phenyl, benzyl, tolyl, and o-xylyl. In Structure A and throughout the description, the term "alkyenyl" denotes a group which connects the two nitrogen atoms to form a bridge and has from 2 to 20 or from 2 to 12 or from 2 to 6 carbon atoms and may connect an atom or atoms within a ring of atoms. Exemplary alkyenyl groups include, but are not limited to, —(CH$_2$)$_2$—, —(CH$_2$)$_3$—, —CH(Me)CH$_2$—, —CH$_2$CH(Me)- wherein "Me" is methyl. In Structure A and throughout the description, the term "alkoxy" denotes an alkyl group that is linked to an oxygen atom (e.g., R—O) and may have from 1 to 20, or from 1 to 12, or from 1 to 6 carbon atoms. Exemplary alkoxy groups include but are not limited to methoxy (—OCH$_3$) and ethoxy group (—OCH$_2$CH$_3$). In certain embodiments, one or more of the alkyl group, aryl group, and/or alkoxy group may be substituted or unsubstituted or have one or more atoms or group of atoms substituted in place of a hydrogen atom. Exemplary substituents include, but are not limited to, oxygen, sulfur, halogen atoms (e.g., F, Cl, I, or Br), nitrogen, and phosphorous.

In one embodiment, $R^4$ is an alkyenyl bridge such as, but not limited to, a group containing 2 or 3 carbon atoms, thereby making a five- or six-member coordinating ring to the metal center. Substituent $R^4$ may be a linear alkyenyl bridge or a branched alkyenyl bridge. In one embodiment, $R^4$ is a linear alkyenyl bridge such as, but not limited to, —(CH$_2$CH$_2$)— and —(CH$_2$CH$_2$CH$_2$)—. In another embodiment, $R^4$ is a branched alkyenyl bridge such as, but not limited to, —CH(Me)CH$_2$— and —CH$_2$CH(Me)-. The term "Me" as used herein denotes a methyl group. In this or other embodiments, any one or more of substituents $R^1$, $R^2$, $R^3$, $R^5$, and $R^6$ can be connected to form a ring. In this or other embodiments, the ring may further comprise carbon, oxygen, and/or nitrogen atoms.

The group 2 metal-containing polydentate β-ketoiminates are prepared in a reaction mixture comprising tridentate ketoimines represented by the following Structure B:

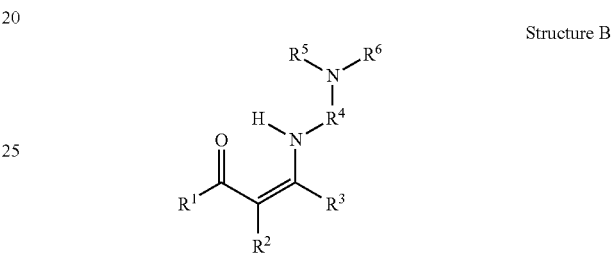

Structure B

In structure B, any one of substituents $R^1$, $R^2$, $R^3$, $R^4$, $R^5$, and $R^6$ is each independently the same as that described above for Structure A.

In the process described herein, at least a portion of the reaction between the group 2 metal and the tridentate ketoimine ligand occurs in the presence of at least one alcohol reagent. In this regard, the complete alcohol charge, or a portion thereof, may be added prior to the onset of reaction, continuously during the reaction step, or a combination thereof. Suitable alcohols include those having the following formula I: $R^7OH$. In formula (I), $R^7$ is an aryl or alkyl moiety comprising from 1 to 20, or from 1 to 12, or from 1 to 6 carbon atoms which be linear, branched, or cyclic such as, but not limited to, methyl, ethyl, propyl, butyl, hexyl, heptyl, octyl, nonyl, decyl, undecyl, dodecyl, and isomers thereof. In certain embodiments, the alcohol can be n-butanol, isopropanol, ethanol, n-propanol, methanol, propanol, isobutanol, pentanol, isoamylalcohol, 2-ethyl-1-hexanol, 2-methyl-1-butanol and combinations thereof. Further alcohol reagents include oligomeric or polymeric alcohols or polyols such as, but not limited to, poly(tetrahydrofuran), poly(propylene glycol), 1,4-butanediol, and combinations thereof. Further exemplary alcohol reagents include those compounds having the following formula (II): $(OH)_nR^8$, where $R^8$ can be any aryl, any linear alkyl, branched alkyl, cyclic alkyl, or a combination of alkyl and/or alkenyl groups, which may be substituted or unsubstituted, and n is the number of attached hydroxyl groups. The term "substituted" as used herein means that the alkyl and/or alkenyl groups may contain one or more other elemental atoms, such as oxygen, nitrogen, sulfur and/or other atoms besides carbon atoms. In certain embodiments, one or more of the alkyl and/or alkenyl groups may be substituted with oxygen atoms. Examples of suitable $R^8$ groups may include, but not be limited to, —(CH$_2$)$_{11}$—CH3, —CH$_2$—CH$_2$—CH$_2$—, —[CH$_2$—CH$_2$—CH$_2$—O]$_m$—CH$_2$—CH$_2$—CH$_2$—CH$_2$—, and —[CH$_2$—CH$_2$—O]$_m$—CH$_2$—CH$_2$—, where m refers to the number of repeat units. Of the foregoing, it is preferred that the alcohol reagent within the reaction mixture should be easily removed from the end product mixture without damaging the end product. In alternative embodiments, the alcohol may be present within the end product mixture in an amount that is 5 weight percent of the end product mixture or less, or 0.5 weight percent of the end product mixture or less. The amount of the alcohol present in the reaction mixture may range from 0.1 to 5.0, per mole of group 2 metal M, preferably a ratio of alcohol to metal M of 2.0.

In certain embodiments, the reaction mixture further comprises one or more solvents. Examples of suitable solvents include organic solvents, such as but not limited to, hexane, benzene, toluene, tetrahydrofuran (THF), ether and acetone. In certain embodiments, it is preferred that the solvent or mixture thereof be selected such that the one or more of the reagents, reaction product, or combinations thereof in the reaction mixture are at least partially soluble. In other embodiments, the alcohol within the reaction mixture acts as both a reagent and a solvent.

In one particular embodiment of the method described herein, group 2 metal-containing polydentate β-ketoiminates are prepared in a reaction mixture comprising a pure group 2 metal, a tridentate ketoimine ligand, and an alcohol reagent in an organic solvent or a mixture of organic solvents. In certain embodiments, the metal and the tridentate ketoimine ligand are added in the organic solvent and then the alcohol is added. In this or other embodiments, the alcohol is added to the reaction mixture "portion wise" to avoid sudden exothermal reaction. The term "portion wise" as used herein means that a portion of the total amount of the alcohol—either pure or diluted with the organic solvent—is added into the reaction vessel containing the reaction mixture (e.g., metal, the tridentate ketoimine ligand, and the organic solvent) via an additional funnel until the whole amount of alcohol is added. In this regard, the amount of alcohol is added incrementally in portions to prevent a sudden exothermic reaction. In certain embodiments, each portion can range from, for example, 10 milliliter (ml) to 100 ml. However, the amount of the portion of alcohol charged into the reaction mixture can vary depending upon the scale of production. In this or other embodiments, the reaction mixture is refluxed at the boiling point of the organic solvent. In one particular embodiment, it was found that refluxing a reaction mixture comprising a pure metal, a tridentate ketoimine ligand, one or more alcohols such as IPA, and a solvent such as tetrahydrofuran (THF), followed by filtration and removal of all volatiles provide target complexes in good yield such as that shown in Equation 4:

Equation 4

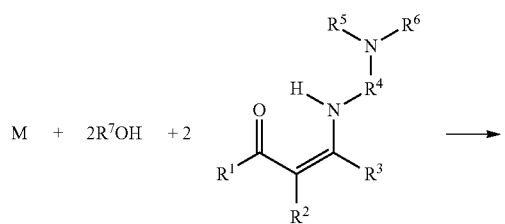

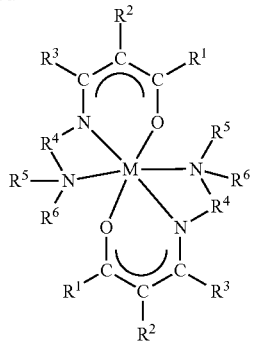

The reaction mixture is exposed to conditions sufficient to provide an end-product mixture containing the group 2 metal-containing polydentate β-ketoiminates. There are a number of ways that the process described herein can be conducted. In certain preferred embodiments, the reaction mixture is heated to a temperature and for a time sufficient to react the reagents contained therein and form an end product mixture. Depending upon the reagents contained within the reaction mixture, the reaction temperature may range from room temperature to 200° C., or at the refluxing temperature or the boiling point of the solvent employed. The reaction time may range from about 0 hours or instantaneous to about 100 hours, or from about 0 to about 60 hours, or from about 4 to about 48 hours. In certain embodiments, the volatiles after reaction may be removed from the end product mixture by standard procedures such as distillation, chromatography, recrystallization, and/or titration. In this or other embodiments, the amount of unreacted materials present within the end product mixture may be sufficiently low (e.g., 5% weight percent of end product mixture or less) due to the volatility of the materials or may remain within the end product mixture because the materials are acceptable impurities within the product.

In one embodiment, the reaction mixture is allowed to react at appropriate temperature and pressure under conditions of total reflux for sufficient time to achieve a significant reaction of the group 2 metal with the alcohol, the polydentate ketoimine, or both. This conversion is sufficient once the concentration of ketoimine in the reactor is reduced to the point where its volatility is no longer an issue in terms of operability or yield.

The teachings of the process described herein has applicability for large scale (production rates in excess of 1000 standard liters), medium bench scale (production rates between 1000 to 10 standard liters), small scale (production rates less than 10 standard liters), and everything in between.

Examples of metal-containing polydentate β-ketoiminate that can be prepared using the method described herein include, but are not limited to, bis(2,2-dimethyl-5-(dimethylaminoethyl-imino)-3-hexanonato-N,O,N')strontium, bis(2,2-dimethyl-5-(1-dimethylamino-2-propylimino)-3-hexanonato-N,O,N')strontium, bis(2,2-dimethyl-5-(1-ethylmethylaminoethyl-imino)-3-hexanonato-N,O,N') strontium, bis(2,2-dimethyl-5-(1-methyethylamino-2-propylimino)-3-hexanonato-N,O,N')strontium, bis(2,2-dimethyl-5-(1-diethylaminoethyl-imino)-3-hexanonato-N,O,N')strontium, and bis(2,2-dimethyl-5-(1-diethylamino-2-propylimino)-3-hexanonato-N,O,N')strontium.

The process described herein may be described using certain alphabetical letters such as in the Summary of the Invention and in the Claims. This is not meant to imply chronological order. Indeed, unless otherwise specified, the method or process steps may be conducted in a variety of different orders, e.g., concurrently, sequentially, etc.

The process described herein will be illustrated in more detail with reference to the following Examples, but it should be understood that the process is not deemed to be limited thereto.

Comparable Example 1

Synthesis of bis(2,2-dimethyl-5-(dimethylaminoethyl-imino)-3-hexanonato-N,O,N')strontium employing strontium amide 40.0 g (0.066 mol) of $Sr(N(SiMe_3)_2)_2 \cdot 2THF$ was loaded in a 500 mL Schlenk flask with 100 ml THF. To this flask was dropwise added 29.0 g (0.14 mol) wax-like 2,2-dimethyl-5-(dimethylaminoethyl-imino)-3-hexanone in 100 mL of THF. The resulting light yellow clear solution was stirred at room temperature over night. All volatiles were then removed under vacuum to give a yellow solid which was dissolved in 100 mL of hot hexanes. GC/MS analysis of the trapped volatile liquid indicated it contained THF and by-product hexamethylsilylamine. GC/MS of the yellow solid dissolving in THF revealed there is only 2,2-dimethyl-5-(dimethylaminoethyl-imino)-3-hexanone besides THF, suggesting the solid contains the tridentate β-ketoiminate ligand. The hexanes solution was then concentrated to about 30 mL to precipitate white crystals on the bottom. The flask was kept at −20° C. to afford more colorless crystals. 26.1 g of the crystals was collected and dried under vacuum. The yield is 77% on the basis of strontium.

Elemental analysis: calculated for $C_{24}H_{46}N_4O_2Sr$: C, 56.49; N, 10.98; H, 9.09. Found: C, 56.34; N, 11.32; H, 8.91. $^1H$ NMR (500 MHz, $C_6D_6$): δ=5.16 (s, 2H), 2.97 (t, 4H), 2.26 (b, 4H), 1.89 (s, 12H), 1.77 (s, 6H), 1.37 (s, 18H).

Example 1

Synthesis of bis(2,2-dimethyl-5-(dimethylaminoethyl-imino)-3-hexanonato-N,O,N')strontium employing pure Sr metal and isopropanol To 44.30 g (505.63 mmol) strontium metal, was added 214.69 g (1011.26 mmol) 2,2-dimethyl-5-(dimethylaminoethyl-imino)-3-hexanone in 175 mL THF directly. Addition of 60.78 g (1011.26 mmol) isopropanol was then carried out slowly via an addition funnel. The reaction flask was equipped with condenser and vented under argon source. The reaction mixture was refluxed for 16 hours after which it became a solution with small amount of particle on bottom of the flask. Cooled reaction to room temperature and filtered through a thin layer of Celite (512 medium) on top of medium porosity frit. Orange-yellow filtrate was pumped under vacuum over night giving rise to a yellow solid weighing 250 g with a crude yield of 97%. Recrystalization from hexanes provides pure product which is confirmed by the proton NMR and TGA to be the same compound as described in Comparable Example 1.

Comparable Example 2

Synthesis of bis(2,2-dimethyl-5-(1-dimethylamino-2-propylimino)-3-hexanonato-N,O,N')strontium employing strontium amide To a solution of 1 g (1.81 mmol) $Sr(N(SiMe_3)_2)_2 \cdot (THF)_2$ in 10 mL, THF was added to 0.82 g (3.62 mmol) 2,2-dimethyl-5-(1-dimethylamino-2-propylimino)-3-hexanone in 10 mL of THF dropwise at room temperature. The reactive mixture was stirred for 16 hours. THF was evaporated off under vacuum to provide an off-white solid that was taken up as a solution in hexanes. Hexanes were removed to provide a solid which was recrystallized in pentane at room temperature. 0.48 g of clear needle-like crystals were obtained (50% yield based on Sr).

Elemental analysis: calculated for $C_{26}H_{50}N_4O_2Sr$: C, 58.01; N, 10.40; H, 9.36. Found: C, 56.07; N, 10.10; H, 8.86. $^1H$ NMR (500 MHz, $C_6D_6$): δ=5.12 (s, 1H), 3.42 (m, 1H), 3.32 (t, 1H), 1.96 (b, 2H), 1.83 (s, 6H), 1.72 (b, 2H), 1.41 (s, 9H), 0.94 (d, 3H).

Example 2

Synthesis of bis(2,2-dimethyl-5-(1-dimethylamino-2-propylimino)-3-hexanonato-N,O,N')strontium employing pure Sr metal and iso-propanol To 43.42 g (495.55 mmol) of strontium metal in 250 mL THF was added 179.48 g (792.88 mmol) 2,2-dimethyl-5-(1-dimethylamino-2-propylimino)-3-hexanone directly followed by addition of 60.70 mL (792.88 mmol) isopropanol. The reaction mixture was refluxed for 16 hours and upon completion the reaction was an amber-red solution and was left to cool to room temperature. The reaction mixture was filtered through a thin layer of medium grade Celite on top of a medium porosity frit. THF was pumped off from the filtrate under vacuum which provided a viscous deep red oil. The oil was dissolved in hexanes and pumped under vacuum again as a means to pump off residual THF. The product remained a tar like oil weighing 240.04 g with a yield of 90%. Recrystalization from octane provides pure product which is confirmed by the proton NMR and TGA to be the same compound as described in Comparable Example 2.

Example 3

Synthesis of bis(2,2-dimethyl-5-(dimethylaminoethyl-imino)-3-hexanonato-N,O,N')strontium employing pure Sr metal and tert-butanol To 2.02 g (23.05 mmol) of strontium metal pieces in 75 mL of THF was added 8.68 g (46.11 mmol) of tert-butanol directly followed by 10.44 g (46.11 mmol) of 2,2-dimethyl-5-(1-dimethylamino-2-propylimino)-3-hexanone in 50 mL THF via canula. Reaction was refluxed for 3 days after which it became a grey-green suspension. Reaction was allowed to cool and was filtered. Filtrate was evaporated under reduced pressure to a beige waxy solid weighing 11.0 g with a crude yield of 94%. Recrystalization from hexanes provides pure product which is confirmed by the proton NMR and TGA to be the same compound as described in Comparable Example 2.

The invention claimed is:

1. A method for preparing a group 2 metal-containing polydentate β-ketoiminate represented by the following structure A:

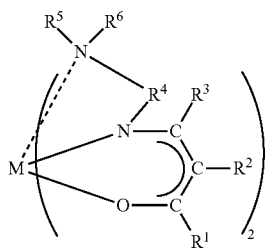

Structure A wherein M is a metal selected from the group consisting of Mg, Ca, Sr, and Ba; $R^1$, $R^3$, $R^5$, and $R^6$ are independently selected from an alkyl group, a fluoroalkyl group, a cycloaliphatic group, and an aryl group; $R^2$ is selected from a hydrogen atom, an alkyl group, an alkoxy group, a cycloaliphatic group, and an aryl group; and $R^4$ is an alkyenyl bridge, wherein the method comprises:

reacting M in a reaction mixture comprising a tridentate ketoimine ligand and an alcohol selected from the group consisting of methanol, ethanol, n-propanol, iso-propanol, n-butanol, sec-butanol, iso-butanol, n-pentanol, neo-pentanol, and combinations thereof, for a reaction time of from about 4 to about 48 hours to obtain the group 2 metal-containing polydentate β-ketoiminate at a yield greater than 80%, wherein the tridentate ketoimine ligand comprises a compound represented by the following structure B:

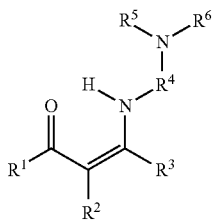

Structure B wherein $R^1$, $R^3$, $R^5$, and $R^6$ are independently selected from an alkyl group, a fluoroalkyl group, a cycloaliphatic group, and an aryl group; $R^2$ is selected from a hydrogen atom, an alkyl group, an alkoxy group, a cycloaliphatic group, and an aryl group; and $R^4$ is an alkyenyl bridge.

2. The method of claim 1 wherein M comprises strontium.

3. The method of claim 1 wherein the molar ratio of M to the alcohol in the reaction mixture ranges from about 0.1 to 5.

4. The method of claim 1 wherein the reaction mixture further comprises an organic solvent.

5. The method of claim 4 wherein the organic solvent comprises toluene and hexane.

6. The method of claim 4 wherein the organic solvent comprises tetrahydrofuran.

7. The method of claim 4 wherein the reacting step is carried out in the presence of the organic solvent wherein at least one of the tridentate ketoimine ligand and the alcohol is at least partially soluble therein.

8. The method of claim 4 wherein the metal and the tridentate ketoimine ligand are added in the organic solvent and then the alcohol is added.

9. The method of claim 8 wherein the alcohol is added to the reaction mixture portion wise to avoid sudden exothermal reaction.

10. The method of claim 4 wherein the reaction mixture is refluxed at the boiling point of the organic solvent.

11. The method of claim 1 wherein the metal-containing polydentate β-ketoiminate comprises bis(2,2-dimethyl-5-(dimethylaminoethyl-imino)-3-hexanonato-N,O,N')strontium.

12. The method of claim 1 wherein the metal-containing polydentate β-ketoiminate comprises bis(2,2-dimethyl-5-(1-dimethylamino-2-propylimino)-3-hexanonato-N,O,N') strontium.

13. The method of claim 1 wherein the metal-containing polydentate β-ketoiminate comprises bis(2,2-dimethyl-5-(1-ethylmethylaminoethyl-imino)-3-hexanonato-N,O,N')strontium.

14. The method of claim 1 wherein the metal-containing polydentate β-ketoiminate comprises bis(2,2-dimethyl-5-(1-methyethylamino-2-propylimino)-3-hexanonato-N,O,N') strontium.

15. The method of claim 1 wherein the metal-containing polydentate β-ketoiminate comprises bis(2,2-dimethyl-5-(1-diethylaminoethyl-imino)-3-hexanonato-N,O,N')strontium.

16. The method of claim 1 wherein the metal-containing polydentate β-ketoiminate comprises bis(2,2-dimethyl-5-(1-diethylamino-2-propylimino)-3-hexanonato-N,O,N')strontium.

17. The method of claim 1 wherein the alcohol is iso-propanol.

\* \* \* \* \*